(12) United States Patent
Doan et al.

(10) Patent No.: US 6,366,820 B1
(45) Date of Patent: Apr. 2, 2002

(54) INTERCONNECTION TECHNIQUE BETWEEN A CABLE CONDUCTOR AND AN ELECTRODE OF AN IMPLANTABLE MEDICAL DEVICE

(75) Inventors: Phong D. Doan, Stevenson Ranch; Kerwyn Schimke, Simi Valley; Sergey Safarevich, Valencia, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/516,622

(22) Filed: Mar. 1, 2000

(51) Int. Cl.$^7$ ................................................. A61N 1/05
(52) U.S. Cl. .......................................... 607/122; 29/825
(58) Field of Search ........................... 29/825; 174/68.1;
600/372, 373, 374, 377, 378, 379, 394;
607/2, 4, 5, 9, 36, 37, 115, 116, 117, 118, 119, 122

(56) References Cited

U.S. PATENT DOCUMENTS

| | | | |
|---|---|---|---|
| 4,105,037 A | 8/1978 | Richter et al. | 128/419 P |
| 4,469,104 A | 9/1984 | Peers-Trevarton | 128/419 P |
| 4,712,557 A | 12/1987 | Harris | 128/419 P |
| 5,012,807 A | 5/1991 | Stutz, Jr. | 128/419 P |
| 5,016,646 A | 5/1991 | Gotthardt et al. | 128/784 |
| 5,067,903 A | 11/1991 | Szyszkowski | 439/55 |
| 5,103,818 A | 4/1992 | Maston et al. | 128/419 P |
| 5,235,742 A | 8/1993 | Szyszkowski | 29/856 |
| 5,282,841 A | 2/1994 | Szyszkowski | 607/36 |
| 5,458,629 A | 10/1995 | Baudino et al. | 607/116 |
| 5,571,146 A | 11/1996 | Jones et al. | 607/37 |
| 5,649,974 A * | 7/1997 | Nelson et al. | 607/122 |
| 5,650,759 A | 7/1997 | Hittman et al. | 333/182 |
| 5,676,694 A * | 10/1997 | Boser et al. | 607/122 |
| 5,869,804 A | 2/1999 | Mueller et al. | 219/121.64 |
| 5,871,514 A | 2/1999 | Wiklund et al. | 607/36 |
| 5,871,515 A | 2/1999 | Wiklund et al. | 607/36 |
| 5,897,578 A | 4/1999 | Wiklund et al. | 607/36 |
| 5,919,215 A | 7/1999 | Wiklund et al. | 607/36 |
| 6,185,463 B1 * | 2/2001 | Baudino | 607/119 |

* cited by examiner

*Primary Examiner*—Jeffrey R. Jastrzab
*Assistant Examiner*—Frances P. Oropeza

(57) ABSTRACT

A method of joining an electrically-conductive elongate member, which may be a multi-strand cable, to an electrically-conductive electrode, possibly for an implantable medical device, requires that the free end of the electrically-conductive member be inserted axially into a longitudinally extending passage of a tubular crimp/weld sleeve. Thereupon, the crimp/weld sleeve is crimped onto the electrically-conductive elongate member to achieve firm engagement between the crimp/weld sleeve and the electrically-conductive elongate member. The crimp/weld sleeve is provided with a radially outward extending prominent member which may be one of a variety of shapes. The electrode is tubular, overlies the outer surface of a longitudinally extending lead body, and is formed with an aperture defined by a rim having a transverse dimension greater than the transverse dimension of the prominent member. The crimp/weld sleeve is received in a recess adjacent the outer peripheral surface of the lead body and the prominent member is inserted into the aperture of the tubular electrode. A laser beam is directed transversely through the aperture of the electrode and onto the prominent member to simultaneously melt the prominent member and the electrode in the region of the aperture and create a mixture of the molten material of both the prominent member and the electrode within the aperture. When operation of the laser beam ceases, a welded connection between the crimp/weld sleeve and the electrode is achieved.

18 Claims, 4 Drawing Sheets

INTERCONNECTION TECHNIQUE BETWEEN A CABLE CONDUCTOR AND AN ELECTRODE OF AN IMPLANTABLE MEDICAL DEVICE

FIELD OF THE INVENTION

This invention relates generally to a technique of joining an electrically-conductive elongate member to an electrically-conductive termination component and, more particularly, to a technique for laser welding the member to the component. In one application, which is not intended to be restrictive of the invention, the novel technique is provided for conductively interconnecting electrical components in an implantable medical device such as a pacemaker, a defibrillator, or the like.

BACKGROUND OF THE INVENTION

Implantable stimulation devices of the type having electrical circuit components are well known in the medical arts. In one particularly common form, the implantable stimulation device comprises a pacemaker unit having an appropriate electrical power supply and related control circuitry for use in electrically stimulating a patient muscle, such as the heart. Such pacemaker units commonly include a hermetically sealed case or housing within which the power supply and control circuitry are protectively encased, in combination with one or more conductive pacemaker leads extending from the housing to the selected muscle structure within the patient. Feed-through terminals on the pacemaker housing accommodate the hermetically sealed passage of electrical conductors to the housing exterior for appropriate connection to the pacemaker lead or leads, typically through the use of so-called connector blocks having set screws or the like for secure lead attachment. The connector blocks and associated feed-through conductors disposed externally of the pacemaker housing are commonly encased within a sealed head structure, such as an insulative head of cast epoxy or the like.

The commonly used form of welding which has heretofore been satisfactory for making connections in implantable stimulation devices between leads and either electrodes or connectors has been resistance welding which unfortunately is operator dependent with many variables including electrode wear, force, and voltage. The inventors and others have come to recognize that laser welding would be desirable for joining small diameter wire to electrodes and connectors, notwithstanding the fact that resistance welders are less expensive than laser welders.

In many instances, the present laser weld design concepts for joining small diameter wire, rod or coiled wire to electrodes and connectors cannot be used to reliably produce a joint. Components made from dissimilar materials having different melting temperatures, normal component fabrication variability, insignificant thermo-mass inherent with certain components, imprecise component alignment during assembly, and unlike materials with distinctly different melting temperatures, are all major factors that affect the reliability and repeatability of weld connections using conventional design concepts.

Typical of more recent developments in this regard is the disclosure presented in U.S. Pat. No. 5,458,629 to Baudino et al. In this instance, a ring electrode may be introduced onto an insulated lead so as to form an isodiametric lead construction. The outer layer of insulation forming the lead body is etched or notched, for example, by being laser etched or physically milled to provide a recess in the lead insulation having a depth corresponding to the thickness of the ring electrode intended to be provided at that location. A ring electrode is introduced onto the notched section on the lead in the form of a C-shaped sleeve adaptable to be introduced onto the notched portion of the lead and subsequently formable into a cylindrical shape when closed into position in the notched portion of the lead so that the edges of the C-shaped sleeve are brought to an abutting as opposed to overlapping relationship. A single conductor is brought through the insulation and aligned with a hole in the C-shaped sleeve to be welded to the sleeve, for example, by laser welding. The final affixation procedure involves laser welding the abutting surfaces of the sleeve together, thereby securely forming a ring electrode isodiametrically within the notch on the electrode.

Following Baudino et al., Mueller et al., in U.S. Pat. No. 5,869,804, disclosed an improved technique of welding an electrically-conductive termination component having first and second opposed surfaces to an electrically-conductive elongate member extending to a terminal end. That method comprises the steps of forming a substantially circular aperture through the termination component and defined by a rim having a diameter substantially equivalent to the transverse dimension of the elongate member. The terminal end of the elongate member is positioned proximate the termination component overlying the rim of the aperture such that the longitudinal axis of the elongate member is generally coplanar with the center of the aperture. Then, a laser beam is directed transversely of the termination component through the aperture therein toward and onto the elongate member to simultaneously melt the elongate member and the termination component in the region of the aperture and create a mixture of the molten material of both the elongate member and the termination component within the aperture. Upon the cessation of operation of the laser beam, the mixture of the molten material solidifies within the aperture and between the termination component and the elongate member to thereby achieve a welded connection between the elongate member and the termination component. In a preferred embodiment, a ball member is formed at an end of the elongate member and the rim of the aperture in the termination component has a diameter smaller than that of the ball member and the ball member is positioned in engagement with the rim of the aperture.

More specifically, in the Mueller et al. patent, either a regular wire, coiled wire or rod, is joined to a larger termination component by means of a laser welded ball and socket joint. The elongate material is fabricated with a spherical end to increase the thermo-mass and laser target assembly. The termination component (i.e., electrode or connector) is fabricated with a target construction hole somewhat smaller than the diameter of the ball. The target hole is located where the joint will be made. Assembly is accomplished by locating the ball in the target hole forming a ball and socket assembly. The assembly is completed by directing the laser through the opposite side of the target hole, directly at the top of the ball. The laser energy melts and fuses the ball and material surrounding the target hole. A capillary effect draws the molten material into the hole resulting in a concave weld fillet.

Other previously successful techniques employing lasers for the effective termination of electrical junctions for implantable medical devices are disclosed in U.S. Pat. No. 5,282,841 to Szyszkowski and U.S. Pat. No. 5,103,818 to Maston et al.

It was with knowledge of the foregoing that the present invention has been conceived and is now reduced to practice.

SUMMARY OF THE INVENTION

The present invention relates to a technique of joining an electrically-conductive elongate member, which may be a multi-strand cable, to an electrically conductive electrode, possibly for an implantable medical device. This technique requires that the free end of the electrically-conductive elongate member be inserted axially into a longitudinally extending passage of a tubular crimp/weld sleeve. Thereupon, the crimp/weld sleeve is crimped onto the electrically-conductive elongate member to achieve firm engagement between the crimp/weld sleeve and the electrically-conductive elongate member. The crimp/weld sleeve is provided with a radially outward extending prominent member which may be one of a variety of shapes. The electrode is tubular, overlies the outer surface of a longitudinally extending lead body, and is formed with an aperture defined by a rim having a transverse dimension greater than the transverse dimension of the prominent member. The crimp/weld sleeve is received in a recess adjacent the outer peripheral surface of the lead body and the prominent member is inserted into the aperture of the tubular electrode. A laser beam is directed transversely through the aperture of the electrode and onto the prominent member to simultaneously melt the prominent member and the electrode in the region of the aperture and create a mixture of the molten material of both the prominent member and the electrode within the aperture. When operation of the laser beam ceases to allow solidification of the mixture of the molten material within the aperture, a welded connection between the crimp/weld sleeve and the electrode is achieved.

In short, a unique protrusion feature is integrated onto the outside surface area of the weld/crimp sleeve. In this design, this feature could be a weld tab, a dome-shaped knob, or a cylindrical post at or near the end of the sleeve away from the crimp zone. In the assembly set-up, the ring electrode is installed over the crimp/weld sleeve and locked in place where the hole of the ring electrode snaps onto the protrusion feature of the sleeve. This provides a reliable set-up for the following step, the laser weld operation. In this manner, a simple cable conductor termination/connection is performed by a simple and reliable connection assembly process.

Accordingly, a primary feature of the present invention is the provision of a technique for reliably welding an electrically-conductive elongate member to an electrically-conductive termination component and, more particularly, for laser welding the member to the component.

Another feature of the invention is a technique for conductively interconnecting electrical components in an implantable medical device such as a pacemaker, a defibrillator, or the like.

Still another feature of the present invention is the provision of such a technique which includes steps of providing an elongated crimp/weld sleeve having a longitudinally extending passage for axially receiving the electrically-conductive elongate member, inserting a free end of the electrically-conductive elongate member into the passage of the crimp/weld sleeve, crimping the crimp/weld sleeve onto the elongate member to achieve firm engagement between the crimp/weld sleeve and the elongate member, forming a radially outward extending prominent member on the crimp/weld sleeve, forming in the termination component an aperture defined by a rim having a transverse dimension greater than the transverse dimension of the prominent member, inserting the prominent member into the aperture of the termination component, directing a laser beam transversely of the termination component through the aperture therein and onto the prominent member to simultaneously melt the prominent member and the termination component in the region of the aperture and create a mixture of the molten material of both the prominent member and the termination component within the aperture, and discontinuing operation of the laser beam to allow solidification of the mixture of the molten material within the aperture to thereby achieve a welded connection between the crimp/weld sleeve and the termination component.

Yet another feature of the present invention is the provision of such a technique wherein the electrically-conductive elongate member includes a lead comprised of a multi-strand cable, each with a free end and wherein each free end of the multi-strand cable is inserted into the passage of the crimp/weld sleeve.

Still a further feature of the present invention is the provision of such a technique wherein the aperture is formed large enough to allow the laser beam to pass therethrough yet small enough to allow the simultaneous melting of the rim of the aperture and the termination component.

Yet a further feature of the present invention is the provision of such a technique wherein the termination component is a cylinder having an inner peripheral surface proximately received on a lead body and wherein the crimp/weld sleeve is positioned within the cylinder such that the longitudinal axis of the crimp/weld sleeve is parallel to a longitudinal axis of the cylinder.

Still another feature of the present invention is the provision of such a technique wherein, in one instance, the prominent member is a radially outward extending cylindrical post, wherein in another instance, a pair of longitudinally-extending spaced-apart cuts through the crimp/weld sleeve define a tab member which, when bent about a transverse fold line, projects radially outward from the crimp/weld sleeve and wherein, in still another instance, the crimp/weld sleeve includes an outer peripheral surface and a peripheral flange lies in a plane extending transverse of the longitudinally extending passage axis and projecting radially outward beyond the outer peripheral surface thereof and wherein the termination component has a transversely extending slot for freely receiving a portion of the peripheral flange therein.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
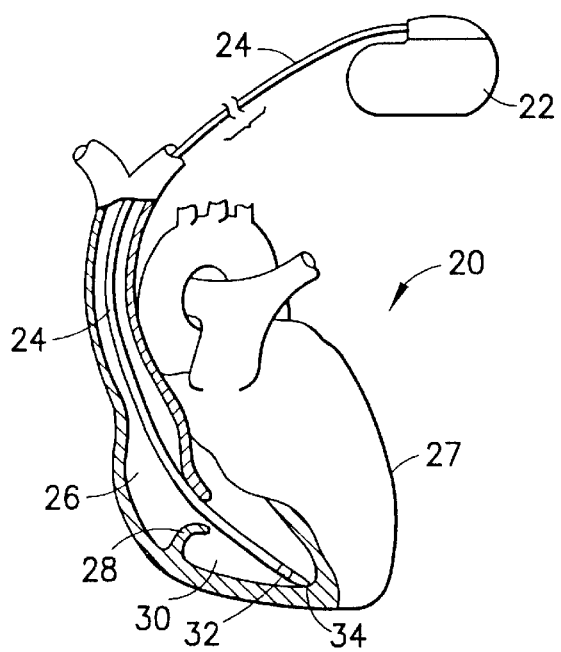
FIG. 1 is a diagrammatic elevation view, partly in section, of a heart pacing system of the type which may utilize the present invention.

Referring to FIG. 1, there is shown in a diagrammatic manner an implantable medical system 20 of the type with which the present invention may be used. Although the present invention will be described with reference to the embodiments shown in the drawings, it should be understood that the present invention may be embodied in many alternative forms of embodiments. In addition, any suitable size, shape or type of elements or materials could be used.

In FIG. 1, a pacemaker 22, representative of a family of implantable medical devices with which the invention may be used, is illustrated as being implanted in the upper chest region of a user. A transvenous endocardial lead body 24 extends from the pacemaker 22 through the right atrium 26 of the heart 27 and through the tricuspid valve 28 into the right ventricle 30. An electrically-conductive electrode 32 at a distal end of the lead 24 is positioned near the location at which a tip end 34 is positioned in engagement with the myocardial tissue of the heart 27.

Figure 2:
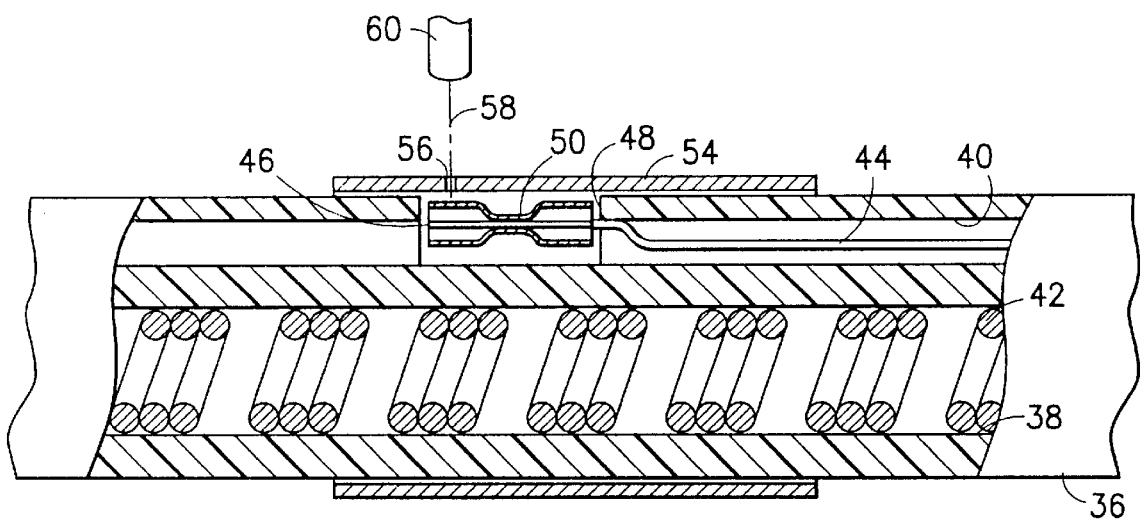
FIG. 2 is a side elevation view, partly cut away and in section, illustrating a known construction of a lead body near the location at which a tip end is engaged with the myocardial tissue of the heart.

FIG. 2 illustrates a known construction of the lead body 24 near the location at which the tip end 34 is engaged with the myocardial tissue of the heart. This known lead body 24 has an outer peripheral surface 36 and a pair of longitudinally extending lumens, 38, 40. In this instance, a bipolar system is depicted with one electrically-conductive elongate member 42 received in the lumen 38 extending to an electrode at the tip end 34 and a second electrically-conductive elongate member 44 received in the lumen 40 extending to a free end 46. The lead body 24 is formed with a recess 48 adjacent the outer peripheral surface 36 and in communication with the lumen 40.

Figure 3:
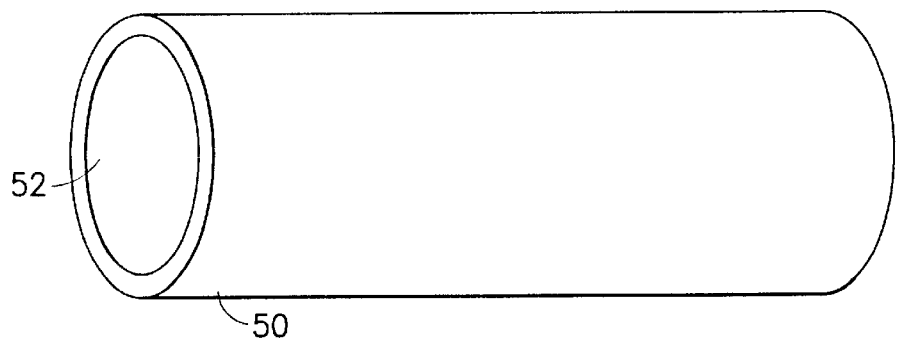
FIG. 3 is a detail perspective view of a known crimp/weld sleeve before its use with a heart pacing system.
Figure 4:
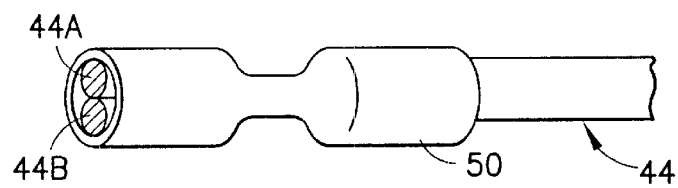
FIG. 4 is a detail perspective view of a known crimp/weld sleeve crimped into engagement with ends of a multi-strand cable.

An elongated crimp/weld sleeve 50 (FIG. 3) with a longitudinally extending passage 52 is positioned in the recess 48 (FIG. 2) for axially receiving the free end of the electrically-conductive elongate member 44 in the passage. So positioned, the crimp/weld sleeve 50 is crimped (FIG. 4) into firm engagement with the elongate member 44. In FIG. 4, the electrically-conductive elongate member 44 is depicted as a multi-strand cable having a pair of ends 44A, 44B although many more ends may actually be present in any one instance. A tubular electrically-conductive termination component 54 or ring electrode, having an aperture 56, is mounted on the lead body 24 so as to overlie the recess 48 with the aperture 56 being coextensive with the crimp/weld sleeve 50. With this known construction, it is customary to direct a laser beam 58 from a suitable laser pumping device 60 transversely of the termination component 54 through the aperture 56 and onto the crimp/weld sleeve 50. The intent is to simultaneously melt the crimp/weld sleeve 50 and the termination component 54 in the region of the aperture 56 and thereby join the two components. Unfortunately, as earlier stated, due to tolerance stack-up of the lead body 24, the elongate member 44, the crimp/weld sleeve 50, and of the ring electrode 54, it is difficult to maintain a good physical contact between the ring electrode 54 and the weld/crimp sleeve 50 which is required for a good and reliable laser weld.

Figure 5:
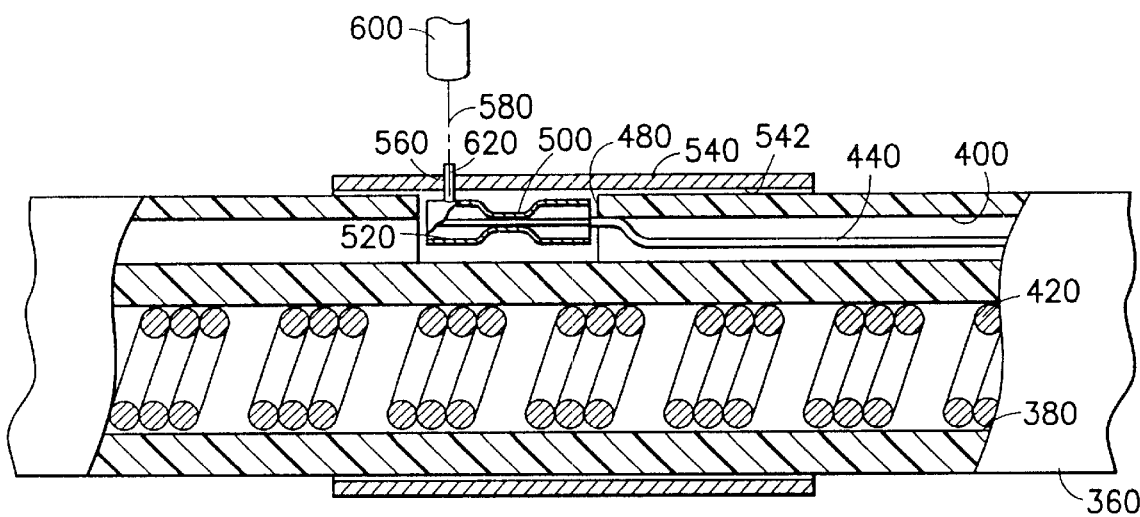
FIG. 5 is a side elevation view, partly cut away and in section, similar to FIG. 2 but illustrating a modified construction utilizing a modified crimp/weld sleeve embodying the present invention.
Figure 6:
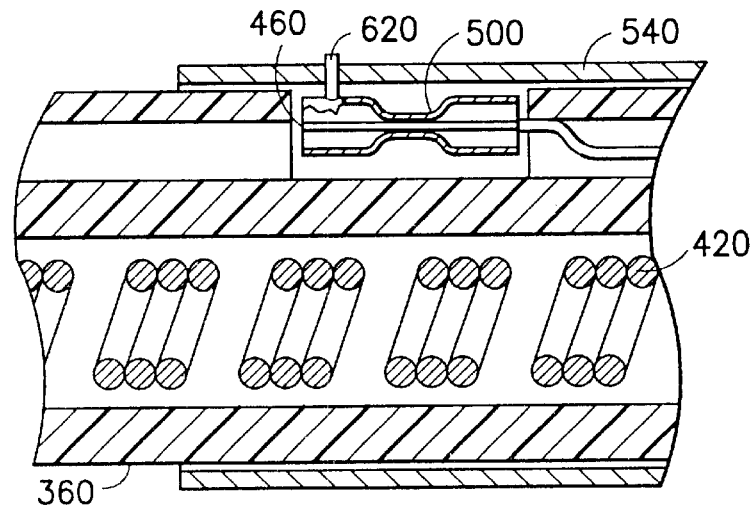
FIG. 6 is an enlarged detail view of certain parts illustrated in FIG. 5.
Figure 7:
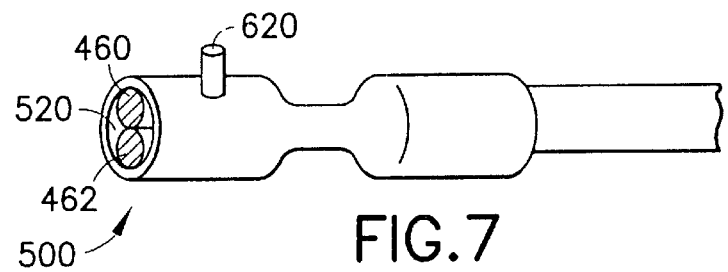
FIG. 7 is a detail perspective view of the crimp/weld sleeve illustrated in FIG. 5 and crimped into engagement with ends of a multi-strand cable.

With the foregoing description as background, turn now, initially, to FIGS. 5, 6, and 7 for a discussion of the present invention in which three digit numbers will be used, adding a third digit to the two digit numbers of the prior art constructions. Also, there will be no redundant description where there is no change in the construction of the invention as compared to the prior art.

In this instance, a crimp/weld sleeve 500 is used in conjunction with a lead body 240 having an outer peripheral surface 360 and longitudinally extending lumens 380, 400. The crimp/weld sleeve 500 is received within a recess 480 adjacent the outer peripheral surface 360 and in communication with the lumen 400. An electrically-conductive elongate member 440 is received in the lumen 400 and has a free end received in a longitudinally extending passage 520 of the elongated crimp/weld sleeve 500 which is then crimped into firm engagement with the elongate member 440. As a major feature of the present invention, the crimp/weld sleeve 500 is formed with a radially outward extending prominent member 620 which may be a post, pin, or other protuberance, affixed to or integral with the outer surface of the crimp/weld sleeve 500. An electrically-conductive termination component 540, or ring electrode, is a tubular member having an inner peripheral surface 542 proximately received on the lead body 240. The crimp/weld sleeve 500 is positioned within the tubular member, that is, the termination component 540, or ring electrode, such that the longitudinal axis of the crimp/weld sleeve 500 is parallel to a longitudinal axis of the termination component 540.

Figure 8:
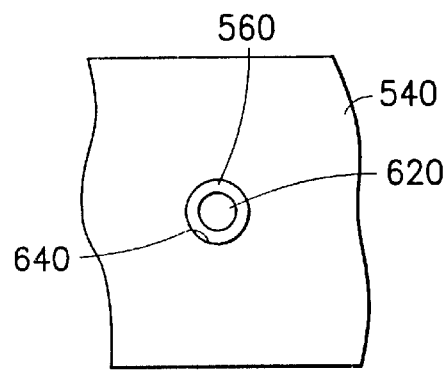
FIG. 8 is a detail top plan view of parts illustrated in FIG. 6.

The termination component 540, or ring electrode, has an aperture 560 defined by a rim 640 (FIG. 8) having a transverse dimension greater than the transverse dimension of the prominent member 620. The prominent member 620 is inserted into the aperture 560 in such a manner that a laser beam 580 from a suitable laser pumping device 600 is directed transversely of the termination component 540 through the aperture 560 and impinges on the prominent member 620 to simultaneously melt the prominent member 620 and the termination component 540 in the region of the aperture 560. This operation creates a mixture of the molten material of both the prominent member 620 and the termination component 540 within the aperture which, when solidified, achieves a strong welded connection between the crimp/weld sleeve 500 and the termination component 540.

While the invention works well when the electrically-conductive elongate member 440 includes a lead comprised of a single strand cable, it is particularly effective with a multi-strand cable, with free ends 460, 462 (FIG. 7) received into the passage 520 of the crimp/weld sleeve 500. Thereupon, the crimp/weld sleeve 500 is crimped into firm engagement with each strand of the multi-strand cable.

The aperture 560 in the termination component 540 is large enough to allow the laser beam 580 to pass through the opening yet small enough to allow the rim 640 of the aperture 560 and the termination component 540 to melt simultaneously. This creates a mixture of the molten material of both the prominent member 620 and the termination component 540 within the aperture 560 after which operation of the laser pumping device 600 is discontinued. This allows solidification of the mixture of the molten material within the aperture 560 to thereby achieve a welded connection between the crimp/weld sleeve 560 and the termination component 540.

Figure 9:
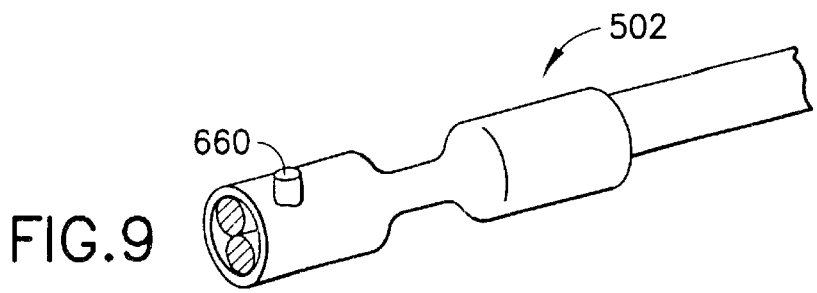
FIG. 9 is a detail perspective view, similar to FIG. 7, illustrating a modified construction of the crimp/weld sleeve.

A variation on the construction of a post or pin as the prominent member 620 illustrated in FIG. 7 is presented in FIG. 9. In this instance, a crimp/weld sleeve 502 includes a prominent member in the form of a radially outward projecting dome-shaped knob 660 which serves in much a similar manner as the post or pin 620.

Figure 10:
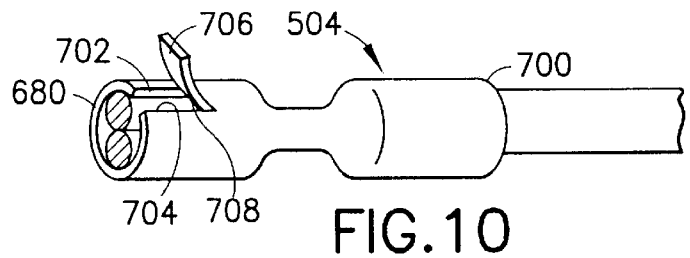
FIG. 10 is a detail perspective view, similar to FIGS. 7 and 9, illustrating another modified construction of the crimp/weld sleeve.
Figure 11:
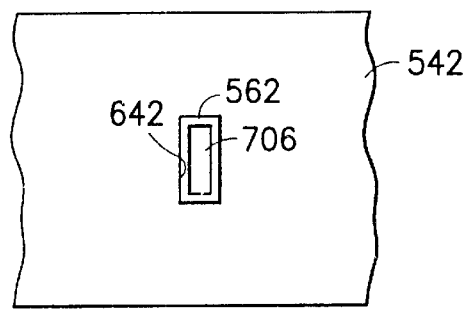
FIG. 11 is a detail top plan view, similar to FIG. 8, illustrating the FIG. 10 construction.

Turn now to FIG. 10 which illustrates still another modified crimp/weld sleeve 504 extending between first and second opposed ends, 680, 700. A pair of longitudinally-extending spaced-apart cuts 702, 704 through the crimp/weld sleeve at the end 680 define a tab member 706 which, when bent about a transverse fold line 708, projects radially outward from the sleeve. In this instance, as seen in FIG. 11, a termination component 542, or ring electrode, has an aperture 562 defined by a rectangular rim 642, as before, having a transverse dimension greater than the transverse dimension of the prominent member 706. The prominent member 706 is inserted into the aperture 562 in such a manner that the laser beam directed transversely of the termination component through the aperture 562 impinges on the prominent member 706 to simultaneously melt the prominent member 706 and the termination component in the region of the aperture 562.

Figure 12:
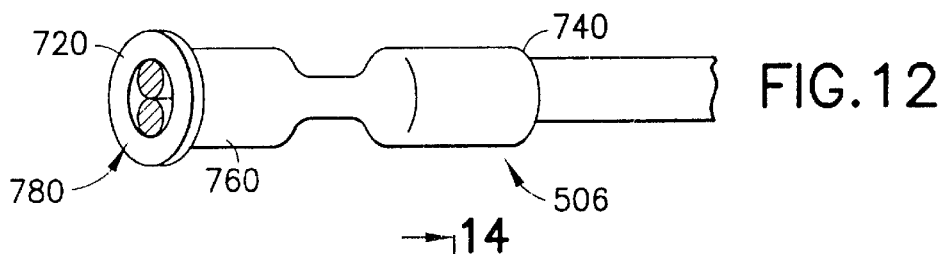
FIG. 12 is a detail perspective view, similar to FIGS. 7, 9, and 10 illustrating still another modified construction of the crimp/weld sleeve.
Figure 13:
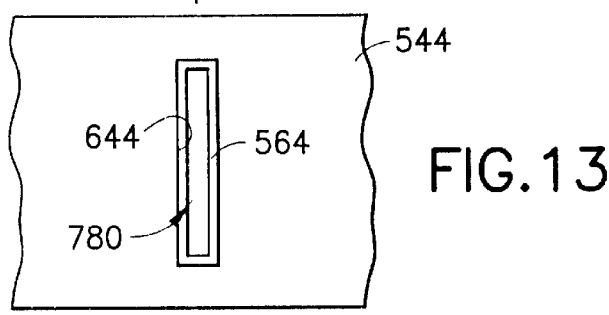
FIG. 13 is a detail top plan view, similar to FIGS. 8 and 11, illustrating the FIG. 12 construction.
Figure 14:
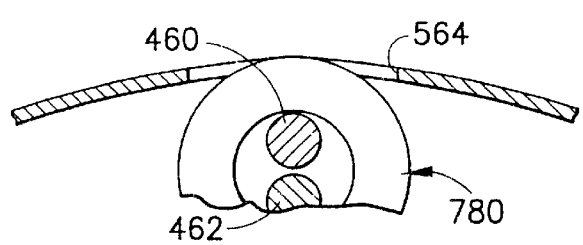
FIG. 14 is a cross section view taken generally along line 14—14 in FIG. 13.

Turn now to FIGS. 12, 13, and 14 which illustrate still another modified crimp/weld sleeve 506 extending between first and second opposed ends, 720, 740 and an outer peripheral surface 760. In this instance, a peripheral flange 780 at the end 720 lies in a plane extending transverse of the longitudinally extending passage axis and projects radially outward beyond the outer peripheral surface 760.

In this instance, as seen in FIGS. 13 and 14, a termination component 544, or ring electrode, has an aperture 564 defined by a transversely extending slot or rectangular rim 644 for freely receiving an arcuate portion of the peripheral flange 780 therein and, as before, having a transverse dimension greater than the transverse dimension of the prominent member. The prominent member is the peripheral flange 780 and an arcuate portion thereof is inserted into the aperture 564 in such a manner that the laser beam, directed transversely of the termination component 544 through the aperture 564, impinges on the prominent member 780 to simultaneously melt the prominent member 780 and the termination component 544 in the region of the aperture 564.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of joining an electrically-conductive elongate member to an electrically-conductive termination component comprising the steps of:

(a) providing an elongated crimp/weld sleeve having a longitudinally extending passage for axially receiving the electrically-conductive elongate member;

(b) inserting a free end of the electrically-conductive elongate member into the passage of the crimp/weld sleeve;

(c) crimping the crimp/weld sleeve onto the elongate member to achieve firm engagement between the crimp/weld sleeve and the elongate member;

(d) forming a radially outward extending prominent member on the crimp/weld sleeve;

(e) forming in the termination component an aperture defined by a rim having a transverse dimension greater than the transverse dimension of the prominent member;

(f) inserting the prominent member into the aperture of the termination component;

(g) directing a laser beam transversely of the termination component through the aperture therein and onto the prominent member to simultaneously melt the prominent member and the termination component in the region of the aperture and create a mixture of the molten material of both the prominent member and the termination component within the aperture; and (h) discontinuing operation of the laser beam to allow solidification of the mixture of the molten material of step (f) within the aperture to thereby achieve a welded connection between the crimp/weld sleeve and the termination component.

2. The method as set forth in claim 1 wherein:

the electrically-conductive elongate member includes a lead comprised of a multi-strand cable, each with a free end; and wherein step (b) includes the step of inserting each free end of the multi-strand cable into the passage of the crimp/weld sleeve.

3. The method as set forth in claim 1 wherein step (e) includes the step of forming the aperture large enough to allow the laser beam to pass therethrough yet small enough to allow the simultaneous melting of the rim of the aperture and the termination component.

4. The method as set forth in claim 1 wherein:

the termination component is a tubular member having an inner peripheral surface proximately received on a lead body; and wherein step (a) includes the step of positioning the crimp/weld sleeve within the tubular member such that the longitudinal axis of the crimp/weld sleeve is parallel to a longitudinal axis of the tubular member.

5. An implantable stimulation device comprising:

an electrically-conductive elongate member having a free end;

an elongated crimp/weld sleeve having a longitudinally extending passage for axially receiving the free end of the electrically-conductive elongate member, the crimp/weld sleeve being crimped into firm engagement with the elongate member;

a radially outward extending prominent member on the crimp/weld sleeve;

an electrically-conductive termination component having an aperture defined by a rim having a transverse dimension greater than the transverse dimension of the prominent member; and wherein the prominent member being inserted into the aperture of the termination component such that a laser beam directed transversely of the termination component through the aperture therein impinges on the prominent member to simultaneously melt the prominent member and the termination component in the region of the aperture and create a mixture of the molten material of both the prominent member and the termination component within the aperture which, when solidified, achieves a welded connection between the crimp/weld sleeve and the termination component.

6. The implantable stimulation device as set forth in claim 5 wherein the electrically-conductive elongate member includes a lead comprised of a multi-strand cable, each with a free end received into the passage of the crimp/weld sleeve, the crimp/weld sleeve being crimped into firm engagement with each strand of the multi-strand cable.

7. The implantable stimulation device as set forth in claim 5 wherein the aperture in the termination component is large enough to allow the laser beam to pass therethrough yet small enough to allow the simultaneous melting of the rim of the aperture and the termination component.

8. The implantable stimulation device as set forth in claim 5 wherein:

the termination component is a tubular member having an inner peripheral surface proximately received on a lead body; and wherein the crimp/weld sleeve is positioned within the tubular member such that the longitudinal axis of the crimp/weld sleeve is parallel to a longitudinal axis of the tubular member.

9. The implantable stimulation device as set forth in claim 5 wherein the prominent member is a radially outward extending cylindrical post.

10. The implantable stimulation device as set forth in claim 5 wherein:

the crimp/weld sleeve includes first and second opposed ends; and wherein a pair of longitudinally-extending spaced-apart cuts through the crimp/weld sleeve define a tab member which, when bent about a transverse fold line, projects radially outward from the crimp/weld sleeve.

11. The implantable stimulation device as set forth in claim 5 wherein the crimp/weld sleeve includes:

first and second opposed ends;

an outer peripheral surface;

a peripheral flange lying in a plane extending transverse of the longitudinally extending passage axis and projecting radially outward beyond the outer peripheral surface therein; and wherein the termination component has a transversely extending slot for freely receiving a portion of the peripheral flange therein.

12. A lead for an implantable stimulation device comprising:

a longitudinally extending lead body having an outer peripheral surface, at least one longitudinally extending lumen, and a recess adjacent the outer peripheral surface and in communication with the lumen;

an electrically-conductive elongate member having a free end received in the longitudinally extending lumen;

an elongated crimp/weld sleeve having a longitudinally extending passage for axially receiving the free end of the electrically-conductive elongate member, the crimp/weld sleeve being crimped into firm engagement with the elongate member;

a radially outward extending prominent member on the crimp/weld sleeve; and an electrically-conductive termination component having an aperture defined by a rim having a transverse dimension greater than the transverse dimension of the prominent member; and wherein the prominent member is adapted to be inserted into the aperture of the termination component such that a laser beam directed transversely of the termination component through the aperture therein impinges on the prominent member to simultaneously melt the prominent member and the termination component in the region of the aperture and create a mixture of the molten material of both the prominent member and the termination component within the aperture which, when solidified, achieves a welded connection between the crimp/weld sleeve and the termination component.

13. The lead of claim 12 wherein the electrically-conductive elongate member includes a lead comprised of a multi-strand cable, each with a free end received into the passage of the crimp/weld sleeve, the crimp/weld sleeve being crimped into firm engagement with each strand of the multi-strand cable.

14. The lead of claim 12 wherein the aperture in the termination component is large enough to allow the laser beam to pass therethrough yet small enough to allow the melting of the rim of the aperture and the termination component simultaneously.

15. The lead of claim 12 wherein:

the termination component is a tubular member having an inner peripheral surface proximately received on a lead body; and wherein the crimp/weld sleeve is positioned within the tubular member such that the longitudinal axis of the crimp/weld sleeve is parallel to a longitudinal axis of the tubular member.

16. The lead of claim 12 wherein the prominent member is a radially outward extending cylindrical post.

17. The lead of claim 12 wherein:

the crimp/weld sleeve includes first and second opposed ends; and wherein a pair of longitudinally-extending spaced-apart cuts through the crimp/weld sleeve define a tab member which, when bent about a transverse fold line, projects radially outward from the crimp/weld sleeve.

18. The lead of claim 12 wherein the crimp/weld sleeve includes:

first and second opposed ends;

an outer peripheral surface;

a peripheral flange lying in a plane extending transverse of the longitudinally extending passage axis and projecting radially outward beyond the outer peripheral surface there; and wherein the termination component has a transversely extending slot for freely receiving a portion of the peripheral flange therein.

* * * * *